US009422218B2

(12) United States Patent
Schliephake et al.

(10) Patent No.: US 9,422,218 B2
(45) Date of Patent: Aug. 23, 2016

(54) PROCESS FOR RECHARGING THE REACTION TUBES OF A TUBE BUNDLE REACTOR WITH A NEW FIXED CATALYST BED

(71) Applicant: BASF SE, Ludwigshafen (DE)

(72) Inventors: Volker Schliephake, Schifferstadt (DE); Klaus Bott, Ludwigshafen (DE); Rolf-Dieter Becher, Mannheim (DE); Klaus Joachim Mueller-Engel, Stutensee (DE); Jochen Petzoldt, Weisenheim am Berg (DE); Ulrich Cremer, Mannheim (DE); Andreas Raichle, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/737,889

(22) Filed: Jun. 12, 2015

(65) Prior Publication Data

US 2015/0274629 A1 Oct. 1, 2015

Related U.S. Application Data

(62) Division of application No. 12/130,116, filed on May 30, 2008, now Pat. No. 9,126,171.

(60) Provisional application No. 60/941,385, filed on Jun. 1, 2007.

(30) Foreign Application Priority Data

Jun. 1, 2007 (DE) ........................ 10 2007 025 869

(51) Int. Cl.
*B01J 8/06* (2006.01)
*B08B 9/043* (2006.01)
*C07C 51/25* (2006.01)
*B01J 8/00* (2006.01)
*C07C 45/35* (2006.01)

(52) U.S. Cl.
CPC ............ *C07C 51/252* (2013.01); *B01J 8/0045* (2013.01); *B01J 8/06* (2013.01); *B08B 9/0436* (2013.01); *C07C 45/35* (2013.01); *B01J 2208/00761* (2013.01)

(58) Field of Classification Search
CPC ........ B01J 8/06; B01J 8/0045; B08B 9/0436
USPC ...... 562/600, 521, 532; 549/258; 568/469.9, 568/474; 558/435; 422/201, 658, 659
See application file for complete search history.

(56) References Cited

U.S. PATENT DOCUMENTS

| | | |
|---|---|---|
| 4,029,636 A | 6/1977 | Lowry et al. |
| 4,077,912 A | 3/1978 | Dolhyj et al. |
| 4,701,101 A | 10/1987 | Sapoff |
| 5,173,468 A | 12/1992 | Boehning et al. |
| 5,221,767 A | 6/1993 | Boehning et al. |
| 5,677,261 A | 10/1997 | Tenten et al. |
| 5,739,391 A | 4/1998 | Ruppel et al. |
| 5,910,608 A | 6/1999 | Tenten et al. |
| 6,063,728 A | 5/2000 | Hinago et al. |
| 6,069,271 A | 5/2000 | Tanimoto et al. |
| 6,169,214 B1 | 1/2001 | Tenten et al. |
| 6,582,667 B1 | 6/2003 | Ogata et al. |
| 6,888,024 B2 | 5/2005 | Dieterle et al. |
| 6,982,347 B2 | 1/2006 | Dieterle et al. |
| 7,119,227 B2 | 10/2006 | Sakakura et al. |
| 7,144,557 B2 | 12/2006 | Yada et al. |
| 7,157,597 B2 | 1/2007 | Dieterle et al. |
| 7,297,814 B2 | 11/2007 | Yada et al. |
| 7,528,281 B2 * | 5/2009 | Yada ........................ B01J 8/003 562/532 |
| 2004/0181083 A1 | 9/2004 | Proll et al. |
| 2004/0191953 A1 | 9/2004 | Dieterle et al. |
| 2004/0192965 A1 | 9/2004 | Petzoldt et al. |
| 2004/0249000 A1 | 12/2004 | Yada et al. |
| 2004/0250868 A1 | 12/2004 | Yada et al. |
| 2005/0109377 A1 | 5/2005 | Schliephake et al. |
| 2005/0261517 A1 | 11/2005 | Dieterle et al. |
| 2006/0161019 A1 | 7/2006 | DeCourcy et al. |
| 2006/0205978 A1 | 9/2006 | Yunoki et al. |

(Continued)

FOREIGN PATENT DOCUMENTS

| | | |
|---|---|---|
| CN | 1764628 A | 4/2006 |
| DE | 2 351 151 | 4/1974 |

(Continued)

OTHER PUBLICATIONS

Office Action issued May 11, 2015 in Chinese Patent Application No. 200880018376.8 (English translation only).
"Verfahren zur Herstellung von Katalysatorformkörpern, deren Aktivmasse ein Multielementoxid ist", Research Disclosure RD 2005/497012, Sep. 2005, pp. 967-1002.
Ullmann's Encyclopedia of Industrial Chemistry, Wiley-VCH, Weinheim 1985, vol. A1, Acrylic Acid and Derivatives, pp. 161-176.
Ullmann's Encyclopedia of Industrial Chemistry, Wiley-VCH, Weinheim 1985, vol. A1, "Acrolein Methacrolein", pp. 149-160.
Ullmann's Encyclopedia of Industrial Chemistry, Wiley-VCH, Weinheim 1988, vol. A11, Chapter Formaldehyde—Production, pp. 624-631.

(Continued)

*Primary Examiner* — Kamal Saeed
*Assistant Examiner* — Janet L Coppins
(74) *Attorney, Agent, or Firm* — Oblon, McClelland, Maier & Neustadt, L.L.P.

(57) ABSTRACT

A process for recharging the reaction tubes of a tube bundle reactor with a new fixed catalyst bed, in which a heterogeneously catalyzed partial gas phase oxidation of an organic compound had been performed beforehand in a preceding fixed catalyst bed comprising Mo-comprising multielement oxide active compositions to form a steam-comprising product gas mixture, in which, before the recharge, solid deposit which had been deposited on the tube inner walls and comprises molybdenum oxide and/or molybdenum oxide hydrate is brushed away with the aid of a brush.

6 Claims, No Drawings

(56) References Cited

U.S. PATENT DOCUMENTS

| | | |
|---|---|---|
| 2007/0021631 A1 | 1/2007 | Yada et al. |
| 2007/0021632 A1 | 1/2007 | Yada et al. |
| 2007/0032377 A1 | 2/2007 | Hibst et al. |
| 2007/0167648 A1 | 7/2007 | Cremer et al. |
| 2008/0177105 A1 | 7/2008 | Raichle et al. |
| 2008/0187467 A1 | 8/2008 | Dieterle et al. |
| 2008/0216915 A1 | 9/2008 | Yada et al. |
| 2008/0234522 A1 | 9/2008 | Yada et al. |
| 2008/0253943 A1 | 10/2008 | Yoda et al. |
| 2008/0269521 A1 | 10/2008 | Hammon et al. |

FOREIGN PATENT DOCUMENTS

| | | | |
|---|---|---|---|
| DE | 25 50838 | 5/1976 | |
| DE | 44 31 949 A1 | 3/1995 | |
| DE | 198 35247 | 2/1999 | |
| DE | 101 31 297 | 1/2003 | |
| DE | 103 13 208 A1 | 10/2004 | |
| DE | 103 13 211 A1 | 10/2004 | |
| DE | 103 13 213 A1 | 10/2004 | |
| DE | 103 13 214 A1 | 10/2004 | |
| DE | 103 53 617 A1 | 1/2005 | |
| DE | 10 2004 025 445 A1 | 2/2005 | |
| DE | 699 15 952 T2 | 2/2005 | |
| DE | 10 2004 018 267 A1 | 11/2005 | |
| DE | 20 2006 014 116 U1 | 2/2007 | |
| DE | 10 2007 005 606 A1 | 4/2008 | |
| DE | 10 2007 019 597 A1 | 5/2008 | |
| DE | 10 2007 004 961 A1 | 7/2008 | |
| EP | 0 467 144 A1 | 1/1992 | |
| EP | 0 700 893 A1 | 3/1996 | |
| EP | 0 714 700 A2 | 6/1996 | |
| EP | 0 962253 | 12/1999 | |
| EP | 0 990 636 A1 | 4/2000 | |
| EP | 1 106 598 A2 | 6/2001 | |
| EP | 1 192 987 | 4/2002 | |
| EP | 1 262 235 | 12/2002 | |
| EP | 1 388 533 A1 | 2/2004 | |
| EP | 1 471 046 A1 | 10/2004 | |
| EP | 1 695 954 A1 | 8/2006 | |
| EP | 1 734 030 A1 | 12/2006 | |
| JP | 2006-159197 | 6/2006 | |
| NL | WO 9802239 A1 * | 1/1998 | ............ B01J 8/002 |
| WO | 93/00158 | 1/1993 | |
| WO | WO 98/02239 | 1/1998 | |
| WO | WO 03/055835 A1 | 7/2003 | |
| WO | WO 03/057653 A1 | 7/2003 | |
| WO | WO 03/059857 A1 | 7/2003 | |
| WO | WO 03/076373 A1 | 9/2003 | |
| WO | WO 2005/030393 A1 | 4/2005 | |
| WO | 2005/050121 | 6/2005 | |
| WO | WO 2005/082522 A1 | 9/2005 | |

OTHER PUBLICATIONS

Ullmann's Encyclopedia of Industrial Chemistry, Wiley-VCH, Weinheim 1990, vol. A16, "Methacrylic Acid and Derivatives", pp. 443-448.

Ullmann'sS Encyclopedia of Industrial Chemistry, Wiley-VCH, Weiheim 1986, vol. A 5, "Catalyst Deactivation and Regeneration", pp. 361-362.

Ullmann's Encyclopedia of Industrial Chemistry, Wiley-VCH, Weinheim 1985, vol. A1, Acrylonitrille: Production, pp. 178-180.

Zhang, L. Liu, et al., Applied Catalysis A: General, 117, (1994), pp. 163-171.

Informally Speaking, The Formaldehyde Newsletter from Perstorp FormoxTM, published Autumn/Winter 2005, pp. 1-16.

"Summary of the proceedings at Formaldehyde Europe 2006", Helsingborg, Perstorp, Sweden, published May 9-10, 2006, 72 pages.

* cited by examiner

PROCESS FOR RECHARGING THE REACTION TUBES OF A TUBE BUNDLE REACTOR WITH A NEW FIXED CATALYST BED

This application is a divisional of U.S. application Ser. No. 12/130,116 filed May 30, 2007, U.S. Pat. No. 9,126,171, and claims the benefit of U.S. application Ser. No. 60/941,385 filed Jun. 1, 2007 and DE 10 2007 025 869.2 filed Jun. 1, 2007.

DESCRIPTION

The present invention relates to a process for recharging the reaction tubes of a tube bundle reactor with a new fixed catalyst bed for the purpose of performing a new heterogeneously catalyzed partial gas phase oxidation of an organic starting compound in the new fixed catalyst bed, in which, before the recharge of the reaction tubes of the tube bundle reactor with the new fixed catalyst bed in the same reaction tubes, a heterogeneously catalyzed partial preceding gas phase oxidation of an organic compound has been performed in a fixed catalyst bed which was disposed in these reaction tubes and comprised at least shaped catalyst bodies whose active composition is a multielement oxide comprising the element Mo in the oxidized state to obtain a steam-comprising product gas mixture, and the preceding fixed catalyst bed, after this partial oxidation has ended, has been withdrawn from the reaction tubes.

Processes for heterogeneously catalyzed partial gas phase oxidation of organic compounds in fixed catalyst beds which are disposed in the reaction tubes of tube bundle reactors and which comprise at least shaped catalyst bodies whose active composition is a multielement oxide (e.g. multimetal oxide) comprising the element Mo in the oxidized state are known for the preparation of industrial chemicals, for example acrylic acid, acrolein, methacrylic acid, methacrolein, acrylonitrile and methacrylonitrile (cf., for example, WO 2005/030393, DE-A 10 2007 005, DE-A 10 2007 004 961, Research Disclosure RD 2005/497012, EP-A 467144, EP-A 714700, US 2006/0205978 and DE-A 10 2004 025 445). In these heterogeneously catalyzed partial gas phase oxidations, the product gas mixture normally comprises steam, which is firstly generally formed as a by-product of the partial oxidation and secondly is in many cases actually added to the reaction gas input mixture as an inert diluent gas.

A tube bundle reactor is an apparatus which comprises a vertical bundle of reaction tubes surrounded by a reactor jacket, both ends of the individual reaction tubes being open and the upper end of each reaction tube ending sealed into a passage orifice of an upper tube plate sealed at the top into the reactor jacket and the lower end ending sealed into a passage orifice of a lower tube plate sealed at the bottom into the reactor jacket, the exterior of the reaction tubes, the upper and the lower tube plate and the reactor jacket together delimiting the reaction tube surrounding space, and each of the two tube plates being spanned by a reactor hood having at least one orifice. In the performance of a heterogeneously catalyzed partial gas phase oxidation in such a tube bundle reactor, its reaction tubes are charged with a fixed catalyst bed (a fixed catalyst bed is filled into its reaction tubes; a fixed catalyst bed is disposed in its reaction tubes) and a reaction gas input mixture which comprises the organic compound to be oxidized partially and molecular oxygen is fed through the at least one orifice in one of the two reactor hoods, and the product gas mixture which comprises the target product which results through partial gas phase oxidation of the organic compound to be oxidized partially to the desired target product as it flows through the fixed catalyst bed disposed in the reaction tubes is removed via the at least one orifice of the other reactor hood, while at least one (generally liquid) heat exchange medium is conducted around the reaction tubes on the jacket side of the tube bundle reactor. Normally, in the case of use of at least one liquid heat exchange medium, it is conducted around the reaction tubes such that each of the two surfaces of the two tube plates facing one another is wetted by liquid heat exchange medium. The at least one (for example liquid) heat exchange medium is typically conducted into the reaction tube surrounding space with a temperature $T_H^{in}$ and back out of the reaction tube surrounding space with the temperature $T_H^{out}$, where $T_H^{out} \geq T_H^{in}$. In principle, the at least one heat exchange medium may also be conducted through the reaction tube surrounding space in gaseous form or in the boiling state. Examples of such tube bundle reactors and heterogeneously catalyzed partial oxidations performed therein are disclosed, for example, by EP-A 700893, DE-A 4431949, WO 03/057653, EP-A 1695954, WO 03/055835, WO 03/059857, WO 03/076373, DE 69915952 T2, DE-A 10 2004 018267, DE 20 2006 014 116 U1 and DE 102007019597.6, and also the prior art cited in the aforementioned documents.

In general, the components of the tube bundle reactor are manufactured from steel. Useful manufacturing steel is both stainless steel (for example of DIN materials number 1.4541 or material 1.4571) and black steel or ferritic steel (for example DIN materials 1.0481, 1.0315 or material 1.0425). Frequently, all components of the tube bundle reactor are manufactured from the same steel type. The reactor hoods are in many cases manufactured from ferritic steel and plated with stainless steel on their inner side. In some cases, the reactor jacket is also manufactured from a different steel type to the other parts of the tube bundle reactor, since it is possible to use corrugated steel for its production.

The space defined by the exterior of the reaction tubes, the two tube plates and the reactor jacket together, within which the at least one (generally liquid) heat exchange medium is conducted, will be referred to in this document as the reaction tube surrounding space.

In the simplest manner, in the reaction tube surrounding space, only one (preferably liquid) heat exchange medium is conducted (such a procedure is also referred to as a one-zone method in a one-zone tube bundle reactor). It is fed to the reaction tube surrounding space typically at its upper or at its lower end with its entrance temperature $T_H^{in}$ through orifices in the reactor jacket, and conducted back out of the reaction tube surrounding space at the opposite end with an exit temperature $T_H^{out}$ through orifices in the reactor jacket.

Caused by the exothermicity of the gas phase partial oxidation, $T_H^{out} \geq T_H^{in}$ during the performance of the partial oxidation (equality relates to the case of evaporative cooling). With the aid of a heat exchanger, heat is typically withdrawn from a portion or the entirety of the (preferably liquid) heat exchange medium conducted out of the reaction tube surrounding space before it is fed back to the reaction tube surrounding space with the temperature $T_H^{in}$.

In the reaction tube surrounding space, the (preferably liquid) heat exchange medium can in principle be conducted around the reaction tubes in simple cocurrent or countercurrent to the reaction gas mixture flowing in the reaction tubes. However, it can also be conducted around the reaction tubes in a meandering manner with the aid of corresponding deflecting plates, such that only over the entire reaction tube surrounding space does a cocurrent or countercurrent to the flow direction of the reaction gas mixture in the reaction tubes exist. When the heat exchange medium used is liquid under the use conditions, it should, appropriately from an application point of view, have a melting point in the range from 0 to or from 50 to 250° C., preferably from 120 to 200° C.

Examples of useful liquid heat exchange media include melts of salts such as potassium nitrate, potassium nitrite, sodium nitrite and/or sodium nitrate, and also melts of metals such as potassium, sodium, mercury and alloys of different metals. However, it is also possible to use ionic liquids (in which at least one of the oppositely charged ions comprises at least one carbon atom) or heat carrier oils (for example high-boiling organic solvents such as mixtures of Diphyl® and dimethyl phthalate). Examples of useful gaseous heat exchange media include steam under elevated pressure or else flue gases. Evaporative cooling may, for example, also be undertaken with boiling water under pressure.

To improve the selectivity of target product formation, the heterogeneously catalyzed partial gas phase oxidation of an organic compound may, though, also be performed as a multizone method (for example two-zone method) in a multizone tube bundle reactor (for example in a two-zone tube bundle reactor). In this case, (for example two) essentially spatially separate (preferably liquid) heat exchange media (which are normally of the same type) are conducted within the reaction tube surrounding space (these may, for example, be separated by separating tube plates which are installed within the reaction tube surrounding space and have corresponding passage orifices for the reaction tubes).

The reaction tube longitudinal section over which the particular (preferably liquid) heat exchange medium extends represents a temperature or reaction zone (the one-zone tube bundle reactor correspondingly has only one reaction zone).

Within the particular temperature zone, the (preferably liquid) heat exchange medium can be conducted as in the one-zone method (also relative to the flow direction of the reaction gas mixture). For the difference between $T_H^{out}$ and $T_H^{in}$, regarding the individual temperature zone, the statements made with regard to the one-zone method apply in an essentially identical manner.

A graphic distinction between a one-zone and a two-zone method (between a one-zone tube bundle reactor and a two-zone tube bundle reactor) is shown schematically, for example, by the figures of DE 102007019597.6 and the figures of EP-A 1695954. Multizone methods, on the other hand, are described, for example, in documents EP-A 1734030, DE-A 10313214, DE-A 10313219, DE-A 10313211, DE-A 10313208 and in the prior art cited in these documents. They are advantageous in particular when a high loading of the fixed catalyst bed with the organic compound to be oxidized partially is selected. The loading of the fixed catalyst bed with reaction gas mixture or with a reaction gas mixture component is understood to mean the amount of reaction gas mixture or reaction gas mixture component in standard liters (l (STP); the volume that the corresponding amount would theoretically take up in gaseous form at 0° C. and 1 atm) which is conducted through one liter of fixed catalyst bed (pure inert beds are not included) per hour.

The reaction gas input mixture (or else reaction gas entry mixture) itself may, in the different procedures in the tube bundle reactor, be conducted within the reaction tubes either from the top downward or from the bottom upward (i.e. the at least one feed orifice may be disposed either in the upper reactor hood or in the lower reactor hood). The same applies to the conduction of the (preferably liquid) heat exchange medium.

The reaction gas input mixture may, on entry into the reaction tubes, in principle be preheated to the temperature of the heat exchange medium flowing on the corresponding tube plate underside.

The temperature of the reaction gas entry mixture may, on entry into the reaction tubes, also be below this temperature of the heat exchange medium. This is advisable when the reaction tubes, in flow direction of the reaction gas mixture, are charged first with a longitudinal section of shaped bodies which are inert with respect to the partial oxidation before the catalytically active section of the fixed catalyst bed comprising shaped bodies having catalytically active composition begins. As it flows through this inert section, the reaction gas entry mixture may then be heated to the temperature of the heat exchange medium flowing around the corresponding catalytically active reaction tube section. In principle, the reaction gas input mixture (the product gas mixture) may be fed in (removed) through more than one feed orifice (removal orifice) present in the corresponding reactor hood. In general, though, both the feed of the reaction gas entry mixture and the removal of the product gas mixture are each effected through only one orifice in the corresponding reactor hood.

Frequently, a heterogeneously catalyzed partial gas phase oxidation of an organic compound can be connected spatially immediately downstream (in this case, the target product of the preceding partial oxidation is normally the organic compound to be oxidized partially in the downstream partial oxidation) or upstream of a heterogeneously catalyzed partial gas phase oxidation of another organic compound. Especially in these cases, the feeding or removing reactor hood can be reduced to a cylindrical pipe orifice (designed as a cylindrical pipe orifice), which may, for example, form a cylindrical transition to an aftercooler (cf., for example, DE-A 10 2004 018267 and DE 102007019597.6).

Of course, it is also possible for two heterogeneously catalyzed partial gas phase oxidations which represent two successive gas phase partial oxidation steps to be performed in immediate succession in the reaction zones of a multizone tube bundle reactor (for example in a two-zone tube bundle reactor), in which case the charge of the fixed catalyst bed in the reaction tubes of the multizone tube bundle reactor normally changes in a corresponding manner at the transition from one reaction step to the next reaction step (cf., for example, the performance of multistage heterogeneously catalyzed partial gas phase oxidations in the so-called "single reactor" according to EP-A 1388533, U.S. Pat. No. 6,069,271, EP-A 990636, US-A 2006/0161019 and EP-A 1106598). Examples of the performance of such multistage heterogeneously catalyzed partial gas phase oxidations in a multizone tube bundle reactor (for example two-zone tube bundle reactor) are the heterogeneously catalyzed partial gas phase oxidation of propylene to acrylic acid and of isobutene to methacrylic acid.

It is common knowledge that heterogeneously catalyzed partial gas phase oxidations are advantageously performed in those tube bundle reactors whose reaction tubes, within the scope of what is possible, are on the one hand manufactured in a very uniform manner (cf., for example, WO 03/059857, DE-A 20 2006 014 116 U1 and EP-A 1471046) and on the other hand charged with the same fixed catalyst bed in a very uniform manner (cf., for example, U.S. Pat.

No. 4,701,101, EP-A 1466883, WO 03/057653, US-A 2006/245992 and US-A 2002/136678).

According to the teaching of JP-A 2006-142288, the reaction tube inner surface should additionally have a minimum surface roughness in order to ensure a very uniform charge of the reaction tubes with fixed catalyst bed.

It is also known from the prior art that heterogeneously catalyzed partial gas phase oxidations in the reaction tubes of a tube bundle reactor charged with a fixed catalyst bed can be performed over comparatively long periods (up to several years) without the fixed catalyst bed in the reaction tubes having to be renewed (freshly charged) (cf., for example, DE-A 103 50 822, DE-A 10 2004 025 445, EP-A 1 734 030 and the prior art acknowledged in these documents). When the fixed catalyst bed is finally exhausted, the operation of the tube bundle reactor is interrupted and the spent fixed catalyst bed is replaced by a new fixed catalyst bed (the reaction tubes are recharged with a new fixed catalyst bed). Subsequently, the tube bundle reactor is put back into operation and the same or another heterogeneously catalyzed partial gas phase oxidation of an organic compound is performed in the new fixed catalyst bed.

In the given context, U.S. Pat. No. 4,701,101 recommends cleaning the reaction tubes of a tube bundle reactor in which a heterogeneously catalyzed partial gas phase oxidation has been performed over prolonged periods, after it has ended and the fixed catalyst bed has been removed, in their interior by sandblasting "to remove any vestiges of rust or of carbonaceous deposits on the walls of the tubes" (cf. transition from column 1 to column 2 in U.S. Pat. No. 4,701,101), before the reaction tubes of the tube bundle reactor are charged again with a fresh fixed catalyst bed. However, a disadvantage of this procedure is that it is comparatively costly and inconvenient (considerable amounts of sand are required, and subsequently have to be disposed of) and has a comparatively abrasive effect (i.e. the internal diameter of the reaction tubes is increasingly widened (but frequently inhomogeneously over the different reaction tubes and their length) in the case of repeated use of the procedure and as a result loses its adaptation to the selected shaped catalyst bodies used).

Moreover, the method of sandblasting is a very effective method which is capable of removing especially persistent deposit on the inner wall of the reaction tubes which is to be removed, but uniformly efficient use over the entire reaction tube length can be achieved only with comparative difficulty, which is why frequent sandblasting causes the constancy of the reaction tube internal diameter to be lost along its length and, in the case of suboptimal use of the procedure, undesired deposit can remain to a slight extent around the middle part of the reaction tube length (which can be several meters) (such undesired deposit impairs, inter alia, the transfer of the heat of reaction from the reaction tube interior to the heat exchange medium).

As an alternative to U.S. Pat. No. 4,701,101, JP-A 2006-159197 recommends washing the reaction tubes of a tube bundle reactor in which a heterogeneously catalyzed partial gas phase oxidation has been performed over prolonged periods, after it has ended and the fixed catalyst bed has been withdrawn, in their interior with a liquid (preferably water) and subsequently drying them before the reaction tubes of the tube bundle reactor are charged again with a fresh fixed catalyst bed. A disadvantage of this procedure is that it acts only on those wall deposits on the interior of the reaction tubes which are soluble in the wash liquid used. Another disadvantage of this procedure is that the resulting suspensions or solutions are generally corrosive and lead, inter alia, to the formation of fly rust and corroded surfaces (which are, inter alia, also disadvantageous because they are capable of catalyzing full oxidation).

In addition, this procedure is not uncritical in that essentially all fixed bed catalysts are sensitive to contact with liquid phases and generally at least partly lose their activity in the event of such contact. In other words, the final drying of the washed reaction tubes (whose total number generally extends to several thousand) cannot truly be performed quantitatively, so that this results in damage to the new fixed catalyst bed charge (typically, the pores of the active composition surface fill with liquid phase and subsequently empty of their own accord generally only with difficulty, which results in coverage of the active sites of the catalyst surface, which reduces the catalyst performance.

It was therefore an object of the present invention to provide a procedure improved over the prior art procedures described, which has their disadvantages only in reduced form, if at all.

Accordingly, a process has been found for recharging the reaction tubes of a tube bundle reactor with a new fixed catalyst bed for the purpose of performing a new heterogeneously catalyzed partial gas phase oxidation of an organic starting compound in the new fixed catalyst bed, in which, before the recharge of the reaction tubes of the tube bundle reactor with the new fixed catalyst bed in the same reaction tubes, a heterogeneously catalyzed partial preceding gas phase oxidation of an organic compound has been performed in a preceding fixed catalyst bed which was disposed in the reaction tubes and comprised at least shaped catalyst bodies whose active composition is a multielement oxide comprising the element Mo in the oxidized state to obtain a steam-comprising product gas mixture, and the preceding fixed catalyst bed, after this partial oxidation has ended, has been withdrawn from the reaction tubes, wherein, between the withdrawal of the preceding fixed catalyst bed from the reaction tubes and the recharge of these reaction tubes with the new fixed catalyst bed, at least in some of the reaction tubes, a solid deposit (solid film) which comprises molybdenum oxide and/or molybdenum oxide hydrate and has been deposited on their inner wall is brushed away at least partly with the aid of a brush.

Preference is given in accordance with the invention to brushing the reaction tubes when dry, i.e. in the absence of liquid phase.

The background to the inventive procedure is the observation that, in the course of performance of heterogeneously catalyzed partial gas phase oxidations in a fixed catalyst bed which comprises shaped catalyst bodies whose active composition is a multielement oxide comprising the element Mo in the oxidized state, and in which the reaction gas mixture (and hence also the product gas mixture) comprises steam (used from the start onward as inert diluent gas and/or formed only as a partial oxidation by-product), in the course of long-term operation of the heterogeneously catalyzed partial gas phase oxidation, molybdenum oxide (especially molybdenum trioxide and/or its hydrate) and/or hydrates of molybdenum oxides (molybdenum oxide hydrate) gradually escape from the catalytic active composition (for example by sublimation, which is promoted by the presence of steam) and are deposited again on the inner wall of the reaction tube as a thin deposit or film (with a thickness of, for example, up to 0.5 mm). These films, though, have an only comparatively restricted adhesion capacity on the reaction tube inner surface and can therefore be at least partly or completely removed (brushed away) by conventional brushing in an entirely satisfactory manner.

Moreover, the film consisting essentially of molybdenum oxide and/or molybdenum oxide hydrate (the latter term shall also encompass molybdenum hydroxides) on the inside of the reaction tubes protects them from marked rust formation, which is why the comparatively drastic measure of sandblasting to remove significant amounts of rust formed in the course of the partial oxidation can be dispensed with in the inventive cases.

It is also advantageous in this connection that the deposition of molybdenum oxide and/or molybdenum oxide hydrate within the reaction tubes charged with fixed catalyst bed is particularly marked where the undesired formation of carbon deposits is normally particularly problematic. This is typically the case in a limited zone beyond the so-called hotspot of the fixed catalyst bed charge in flow direction. Since heterogeneously catalyzed partial gas phase oxidations are normally markedly exothermic reactions, the temperature of the reaction gas mixture in the course of reactive passage through the fixed catalyst bed is normally different from the temperature of the fluid heat exchange medium flowing around the fixed catalyst bed outside the catalyst tubes. It is typically above the entrance temperature of the heat exchange medium $T_H^{in}$ into the corresponding reaction zone (temperature zone) and passes through an absolute maximum (hotspot maximum) or falls starting from an absolute maximum value (if appropriate via further relative maxima) along a reaction zone. Where comparatively elevated temperatures of the reaction gas mixture are present, not only is the tendency to thermal decomposition of the organic constituents of the reaction gas mixture to form comparatively carbon-rich constituents which are deposited again on the reaction tube inner surface in relatively cold regions increased, but the transfer rate of molybdenum oxide and/or molybdenum oxide hydrate into the gas phase is also increased in these regions, which is why the carbon-like deposits in the inventive case, in contrast to those of U.S. Pat. No. 4,701,101, if at all, generally form where a film of molybdenum and/or molybdenum oxide hydrate has already been deposited, which is why the removal of such carbon-like deposits on the reaction tube inner walls also does not require the comparatively drastic removal method of sandblasting in the inventive cases. Instead, such carbon-like deposits would not, in accordance with the invention, be deposited immediately on the reaction tube inner wall but rather on said already deposited molybdenum oxide and/or molybdenum oxide hydrate films. They are therefore not capable immediately of caking on the reaction tube inner wall but rather, if anything, on the films of essentially molybdenum oxide and/or molybdenum oxide hydrate which adhere comparatively moderately on the reaction tube inner wall, which is why they can likewise be removed by brushing in the inventive case. This is all the more true in that, in the long-term operation of an inventive heterogeneously catalyzed partial gas phase oxidation, the reduction in the activity of the fixed catalyst bed which is established over the operating time is generally counteracted by gradually increasing $T_H^{in}$ of the at least one heat exchange medium. This increase is normally also accompanied by an increase in the hotspot temperatures mentioned, which then typically cause significant thermal decomposition only from exceedance of a limiting temperature. In other words, at a time where a protective film comprising molybdenum oxide and/or molybdenum oxide hydrate has already formed on the reaction tube inner surface.

A full oxidation of an organic compound with molecular oxygen is understood here to mean that the organic compound is converted under the reactive action of molecular oxygen such that all of the carbon present in the organic compound is converted to oxides of carbon and all of the hydrogen present in the organic compound to oxides of hydrogen. All different conversions of an organic compound under the reactive action of molecular oxygen are summarized in this document as partial oxidations of an organic compound.

In particular, partial oxidations shall be understood in this document to mean those conversions of organic compounds under the reactive action of molecular oxygen in which the organic compound to be oxidized partially, after the reaction has ended, comprises at least one oxygen atom more in chemically bonded form than before the partial oxidation was performed.

A diluent gas which behaves essentially inertly under the conditions of the heterogeneously catalyzed gas phase partial oxidation is understood in this document to mean those diluent gases whose constituents in the reaction gas mixture present under the conditions of the heterogeneously catalyzed partial gas phase oxidation—each constituent viewed alone—remain unchanged to an extent of more than 95 mol %, preferably to an extent of more than 99 mol %. They have the task firstly of absorbing part of the heat of reaction and conducting it out of the tube bundle reactor as a constituent of the product gas mixture, and secondly of ensuring that the reaction gas mixture is generally outside the explosive range. Inert diluent gases suitable for heterogeneously catalyzed partial gas phase oxidations relevant in accordance with the invention are, for example, $N_2$, $CO_2$, steam, noble gases and in many cases also saturated hydrocarbons (for example in a partial oxidation of unsaturated organic compounds) or mixtures of all or portions of the aforementioned possible inert diluent gases.

Multielement oxides (frequently multimetal oxides) which comprise the element Mo in the oxidized state shall be understood in this document to mean multielement oxides in which the Mo has a positive oxidation number. The oxidation number of the Mo is understood to mean that charge number that the Mo has when the binding electrons in the (particular) multielement oxide in question are assigned to the more electronegative binding partner in each case (cf. Grundlagen der allgemeinen and anorganischen Chemie [Fundamentals of general and inorganic chemistry], Verlag Sauerländer, Aarau, 1973, pages 73/74).

Particularly frequently, the Mo in multielement oxides relevant in accordance with the invention has the oxidation number+VI.

The reactants present in the reaction gas mixture of a heterogeneously catalyzed partial gas phase oxidation ($O_2$ and the organic compound) are converted as the reaction gas mixture is conducted through the fixed catalyst bed disposed in the reaction tubes during the residence time of the reactants at the catalyst surface.

The reaction temperature in the reaction tubes is controlled, inter alia, by the at least one heat exchange medium conducted within the reaction tube surrounding space.

The reaction tubes in the tube bundle reactor are, as already mentioned, generally manufactured from ferritic steel or from stainless steel, and frequently have a wall thickness of a few mm, for example from 1 to 3 mm. Their internal diameter is usually a few cm, for example from 10 to 50 mm, frequently from 20 to 30 mm. The tube length extends normally to a few meters (a typical reaction tube length is in the range from 1 to 10 m, frequently from 2 to 8 m or to 6 m, in many cases from 2 to 4 m).

Appropriately from an application point of view, the number of reaction tubes (working tubes) accommodated in the tube bundle reactor amounts to at least 1000, frequently at least 3000 or 5000 and in many cases to at least 10 000. Frequently, the number of catalyst tubes accommodated in the tube bundle reactor is from 15 000 to 30 000 or from 40 000 to 50 000. Tube bundle reactors having a number of catalyst tubes above 50 000 are usually the exception. Within the reaction tube surrounding space, the reaction tubes are normally arranged in essentially homogeneous distribution, the distribution appropriately being selected such that the distance of the central internal axes of mutually adjacent reaction tubes (the so-called reaction tube pitch) is from 25 to 55 mm, frequently from 35 to 55 mm. Working tubes are typically distinguished from thermal tubes, as described, for example, by EP-A 873783. While the working tubes are those reaction tubes in which the heterogeneously catalyzed partial gas phase oxidation in the actual sense is performed, thermal tubes serve the purpose primarily of monitoring and of controlling the reaction temperature in the reaction tubes. For this purpose, the thermal tubes normally comprise, in addition to the fixed catalyst bed, a thermowell which is conducted along the center of the thermal tube and is charged merely with a temperature sensor. In general, the number of thermal tubes in a tube bundle reactor is very much smaller than the number of working tubes. Normally, the number of thermal tubes is ≤20.

Advantageously in accordance with the invention, in the process according to the invention, at least in 10% of all reaction tubes, preferably in at least 20% or in at least 30% of all reaction tubes, particularly advantageously in at least 40% or in at least 50% of all reaction tubes, very particularly advantageously in at least 60% or in at least 70% of all reaction tubes and at best in at least 80% or in at least 90% or in 100% of all reaction tubes, between the withdrawal of the preceding fixed catalyst bed from the reaction tubes and the recharge of these reaction tubes with the new fixed catalyst bed, a solid deposit (solid film) which comprises molybdenum oxide and/or molybdenum oxide hydrate and has been deposited on their inner wall is brushed away at least partly with the aid of a brush.

Preferably in accordance with the invention, the relevant solid deposit, in the course of the inventive brushing, is removed from the particular brushed reaction tube to an extent of at least 25% of its weight, more preferably to an extent of at least 50% of its weight or to an extent of at least 75% of its weight and most preferably to an extent of at least 90% by weight or to an extent of at least 95% of its weight, or completely. In this document, a brush shall be understood to mean any shaped body which can be moved through a reaction tube and, in the process, wears away (abrades) the relevant deposit on the reaction tube inner wall. In general, such shaped bodies have a non-smooth surface. Appropriately from an application point of view, they are such that they do not significantly damage the reaction tube inner wall when they are moved through a reaction tube. The longest dimension of such shaped bodies (the longest direct straight line connecting two points on the surface of the shaped body) is normally at least 50% of the internal diameter of the reaction tube to be brushed in accordance with the invention, in most cases even at least 75%, or at least 100%, or at least 125% of this internal diameter. In the simplest case it may, for example, be a pig (for example in the form of a cubic foam cube) with a rough surface which, for example, just touches the inner wall of the relevant reaction tube with its rough surface and, for example, can be driven through the reaction tube to be cleaned using compressed air, for example counter to gravity.

Preferably in accordance with the invention, useful such shaped bodies are primarily, however, conventional brushes, which are normally formed from a base body (for example of wood, metal and/or plastic) and a brush head (the bristles). Useful brush heads for the process according to the invention are mineral fibers (e.g. glass fibers), natural fibers (e.g. animal bristles), synthetic fibers (e.g. nylon), synthetic fibers with abrasive coating (e.g. Thonyl), and also smooth or corrugated metal wires (e.g. ferritic steel, stainless steel, brass, bronze, zinc-plated steel).

Useful brushes useable in principle for a process according to the invention include roller brushes, round brushes, pipeline brushes, conical brushes, cylindrical tube brushes, conical tube brushes, rectangular tube brushes and spiral brushes (the latter being particularly preferred in accordance with the invention).

In brushes with a braided head, the base body is normally a circular blank. For example, wire bundles are inserted into the holes drilled on the edge and then twisted. Their design is generally round.

In the case of punched brushes, head bundles are introduced into the holes of a base body and anchored. Anchoring means are wire loops or specific anchors made of sheet metal.

In circular hole brushes, which are in principle round brushes, the head is pressed in between a tube and a ring. As already stated, their design is always round (height (length) ≤external diameter). Constructed in segments, they can also be designed as rollers (height (length)>external diameter).

In the case of the stiff brushes, the base construction is usually a curved sheet metal strip in whose fold the head is fixed by a holding wire. In principle, the base construction of this brush type may also be produced from plastics. Their designs may, for example, be straight, helical, roll-shaped (wound around a shaft) or freely formed.

In cases favorable in accordance with the invention, the brush body (the base body) is not cut open but rather merely drilled open very finely. Wires are pulled through these bores, around which the bristle bundles are conducted individually. Subsequently, bores are sealed by small stoppers on the end side. This complicated method ensures a very long life of the brush.

It is possible through the brush diameter, inter alia, to additionally control the peripheral speed or the axial speed and hence the performance of the brush. The diameter of the brush and the length of the particular head are determining factors for the result of the inventive reaction tube treatment process. The combination of relatively small brush body diameters and relatively high head length results in comparatively flexible ("soft") brushes whose use ensures particularly gentle surface treatment. A greater brush body diameter in combination with short head lengths (bristle lengths) of the head material gives rise to more aggressive ("harder") brushes which can be used, for example, in the case of relatively severe deposit formation relevant in accordance with the invention.

Advantageously in accordance with the invention, the process according to the invention will be performed such that it begins with a "harder" brush and the process ends with a "softer" brush. This procedure ensures, in a particularly simple manner, that the surface of the reaction tube interior, in the course of inventive brushing, is not scratched and/or not worn away abrasively in the case of repeated use.

Even the requirement profile for the roughness of the reaction tube inner surface according to the teaching of JP-A 2006-142288 can also be satisfied with this procedure over operation of the tube bundle reactor in a simple manner in accordance with the invention over several years.

The head density of a brush is the number of wire tips per surface unit of the base body of the brush. High head densities typically ensure good results on application of the process according to the invention and an increased lifetime of the brush used. A spiral-shaped head (especially in the case of a cylindrical base body (i.e., for example, in the case of a round brush or roller brush or tubular brush)) is, as already stated, particularly preferred for the process according to the invention. Mounted onto a bendable rotation shaft (generally, brushes suitable in accordance with the invention have a one-sided or two-sided shaft attachment), the brush moves effectively of its own accord into the reaction tube to be brushed (in the case of agreement of the sense of rotation of the shaft and sense of rotation of the spiral). It is particularly simple in this way to drive the cleaning brush forwards in the reaction tube to be cleaned. In this case, particularly advantageous angles of inclination of the spiral are from 5 to 50°, preferably from 10 to 40° or from 15 to 25° or from 25 to 35°.

Instead of guiding the brush into the reaction tube on a rotating shaft, the brush can, in a simpler embodiment of the process according to the invention, also be moved to and fro within the tube secured on a pole or on a spring. Instead of a simple head spiral, it is also possible for a round (or roller or tubular) brush suitable in accordance with the invention to be designed with a double or multiple head spiral.

The bristle thickness in brushes suitable according to the invention may, for example, be from 0.08 to 1.20 mm.

Preference is given in accordance with the invention to a bristle thickness (especially in the case of metal wires) which is in the range from 0.1 to 0.5 mm.

In principle, it is advantageous from an application point of view in the process according to the invention when the brush diameter is not greater than the internal width of the reaction tube to be cleaned.

Appropriately from an application point of view, the brush diameter is from 0.1 to 2 mm, frequently from 0.5 to 1.5 mm, below the internal width of the reaction tube to be cleaned (the internal width always relates to the reaction tube free of deposits).

Particularly advantageous in accordance with the invention are cylindrical tube brushes with a spiral head. The cylinder length is advantageously from 4 to 25 cm, particularly advantageously from 6 to 15 cm. The head material used may also be the same material from which the reaction tubes themselves are manufactured. The wire head is preferably smooth and not corrugated. The head length is generally not less than 20% of the reaction tube internal radius and typically not more than 80% of the reaction tube internal radius. A head material which is quite generally favorable in accordance with the invention is, for example, DIN materials 1.4310 and 1.4401. It will be appreciated that it is also possible for this purpose to use DIN materials 1.4301 and 1.4571.

When the brush is driven by means of a shaft in the reaction tube, peripheral speeds typical in accordance with the invention are from 25 to 35 m/sec in the case of a smooth head (especially in the case of metal wire) and from 15 to 25 m/sec in the case of a corrugated head.

The attritus of the reaction tube internal deposit generated in the process according to the invention can, in the simplest embodiment, be collected at the lower end of the reaction tube (it normally falls through the mesh of the support grid for the shaped catalyst bodies). Advantageously, the support grid is removed before the inventive reaction tube cleaning.

In an embodiment of the inventive procedure which is preferred from an application point of view, the attritus generated by the brushing is sucked out of the particular reaction tube as soon as it is formed. Such a procedure is preferable from safety points of view. In this case, the at least one suction orifice may be mounted in the base body of the brush and/or in a separate elastic suction hose introduced into the reaction tube parallel to the brush. In the case of such a suction embodiment of the process according to the invention, the reaction tube orifice is closed and normally sealed in the upper tube plate of the tube bundle reactor in the course of performance of the process, and the shaft which drives the brush and/or the suction hose are likewise conducted and sealed in this closure.

The process according to the invention is a comparatively demanding and still complicated process (on average, the inventive cleaning of from 20 to 40 reaction tubes consumes one brush; the inventive cleaning of 22 000 reaction tubes takes about 200 man hours). Nevertheless, it is superior to the prior art processes not least because it can be performed with comparatively good maintenance of the material of the reaction tube wall and nevertheless with high cleaning efficiency. An endoscopic inspection of the reaction tubes gives information about the cleaning action. Furthermore, the inventive procedure can be employed anywhere.

Very particularly advantageously in accordance with the invention, the tube bundle reactor is manufactured from ferritic steel of DIN type 1.0425. For the reactor plates, reaction tubes and reactor hoods, steel of DIN materials number 1.0481 or 1.0315 is frequently also used, and, for the reactor jacket, steel of DIN materials number 1.0345 is in many cases used. That reactor hood through which the reaction gas input mixture flows in is, however, advantageously from an application point of view, plated with austenitic steel (preferably of DIN type 1.4541 or of DIN type 1.4571). Typical plating thicknesses are about 3 mm.

Especially in the case of tube bundle reactors with a relatively large cross section of their tube plates, it is appropriate from an application point of view to leave a region without tubes in the center of the tube bundle reactor, and instead to support the upper tube plate within this region. The statement that the reaction tubes are sealed into the passage orifices in the upper and lower tube plate expresses that no means of passage for the heat exchange medium exists between the reaction tube outer wall and the bore wall (or the wall of the passage orifice, or else shells of the passage orifice). Such sealing can be effected as described, for example, in DE 202006014116 U1. In a corresponding manner, the circumference of the upper and lower tube plate is also incorporated into the reactor jacket of the tube bundle reactor such that no means of passage for the heat exchange medium exists between them. In the upper tube plate is generally disposed, in the case of use of a liquid heat exchange medium, however, a connection to the heat exchange medium pump which ensures degassing of the reaction tube surrounding space and ensures that the liquid heat exchange medium wets the upper tube plate (cf., for example, EP-A 987057). Otherwise, a one-zone tube bundle reactor is preferably configured as described in DE-A 4431949.

The temperature $T_H^{in}$ of the at least one (preferably liquid) heat exchange medium in the heterogeneously catalyzed partial preceding gas phase oxidation of an organic compound is typically in the range from 200 to 500° C., frequently in the range from 250 to 400° C. and in many cases in the range from 250° C. to 310° C.

The steam content of the reaction gas input mixture in the heterogeneously catalyzed partial preceding gas phase oxidation may in principle be 0 (vanishing).

In these cases, it is essential to the invention that $H_2O$ is formed as a by-product of the heterogeneously catalyzed partial preceding gas phase oxidation. Otherwise, the process according to the invention is suitable especially when the steam content of the reaction gas input mixture in the preceding gas phase partial oxidation is ≥0% by volume. It is advantageous especially when this steam content of the reaction gas input mixture is from ≥0.1 to 60% by volume, or from ≥0.2 to 50% by volume, or from ≥0.3 to 40% by volume, or from ≥0.4 to 30% by volume, or from ≥0.5 to 25% by volume, or from ≥0.75 to 20% by volume, or from ≥1 to 15% by volume, or from ≥2 to 10% by volume. Owing to its specific heat capacity, steam is generally an outstanding inert diluent gas for preceding gas phase partial oxidations and in many cases has a beneficial effect on the catalyst activity.

The working pressure in a heterogeneously catalyzed preceding gas phase partial oxidation may be either below standard pressure (for example up to 0.5 bar, the reaction gas mixture is sucked through) or above standard pressure. Typically, the aforementioned working pressure is at values of from 1 to 5 bar, frequently from 1.5 to 3.5 bar. Normally, the working pressure in a preceding gas phase partial oxidation will not exceed 100 bar.

A useful source for the molecular oxygen required for a preceding gas phase partial oxidation in the reaction gas input mixture include air, pure molecular oxygen, air depleted in molecular nitrogen or other mixtures of inert gas and molecular oxygen.

The content in the reaction gas input mixture of the organic compound to be oxidized partially under heterogeneous catalysis, in a preceding gas phase partial oxidation, may be up to 50% by volume or more. Frequently, this content will be from ≥2 to 20% by volume, or from ≥4 to 12% by volume. When the reaction gas input mixture comprises the molecular oxygen in a substoichiometric amount based on the desired partial oxidation, the excess amount of the organic compound to be oxidized partially present in the reaction gas entry mixture may in principle function as an inert diluent gas. When the reaction gas input mixture comprises molecular oxygen in a superstoichiometric amount based on the partial oxidation, the amount is, advantageously from an application point of view, frequently selected such that the composition of the reaction gas input mixture is outside the explosive composition range.

For reasons of a very long catalyst lifetime, the proportion of the molecular oxygen in the reaction gas input mixture of a preceding gas phase partial oxidation will generally appropriately be selected such that the product gas mixture of the preceding gas phase partial oxidation still comprises excess molecular oxygen (for example up to 3% by volume).

The volume flow rate of the heating medium (of the at least one heat exchange medium (preferably a liquid heat exchange medium)) in the reaction tube surrounding space in a preceding gas phase partial oxidation is typically such that the temperature rise (caused by the exothermicity of the reaction) of the (preferably liquid) at least one heat exchange medium, from its entry point into the reactor up to its exit point from the reactor, is from ≥0 to 15° C. or to 10° C., frequently from ≥2 to 8° C., often from ≥3 to 6° C.

The loading of the fixed catalyst bed with the organic compound to be oxidized partially in a preceding gas phase partial oxidation will generally be ≥50 l (STP)/l·h, usually ≥75 l (STP)/l·h, in many cases ≥100 l (STP)/l·h. Usually, this loading will, however, be ≤600 l (STP)/l·h.

The loading of the fixed catalyst bed with reaction gas input mixture in a preceding gas phase partial oxidation will frequently be ≥1500 l (STP)/l·h, or ≥2000 l (STP)/l·h, or ≥2500 l (STP)/l·h, or ≥3000 l (STP)/l·h, or ≥4000 l (STP)/l·h. In general, the aforementioned loading in preceding gas phase partial oxidations is, however, at values of ≤6000 l (STP)/l·h, or ≤5000 l (STP)/l·h.

The conversion of the organic compound to be oxidized partially in a preceding gas phase partial oxidation will typically be ≥50 mol % frequently ≥70 mol %, in many cases ≥80 mol % and often ≥90 mol % (based on single pass of the reaction gas mixture through the fixed catalyst bed). The selectivity of target product formation will typically be ≥70 mol %, frequently ≥80 mol % and in many cases ≥90 mol %.

Otherwise, the boundary conditions of a heterogeneously catalyzed preceding gas phase partial oxidation are, appropriately from an application point of view, overall, normally selected such that the temperature difference between the hotspot maximum of the reaction gas mixture in the individual reaction zones (temperature zones) of the tube bundle reactor and the particular accompanying $T_H^{in}$ of the temperature zone, even in long-term operation, does not generally exceed 80° C. Usually, this temperature difference, even in long-term operation, is ≤70° C., frequently from 20 to 70° C. or to 50° C.; this temperature difference, even in long-term operation, is preferably low.

Moreover, the aforementioned boundary conditions are typically selected such that the "peak-to-salt temperature sensitivity" (cf. definition in EP-A 1106598), especially also in long-term operation, is ≤9° C., but ≤7° C., or ≤5° C., or ≤3° C.

In many cases, in an inventive heterogeneously catalyzed partial preceding gas phase oxidation, in at least 25% by weight, or in at least 50% by weight, or in at least 75% by weight or in the entirety of the shaped catalyst bodies of the fixed catalyst bed disposed in the reaction tubes, the active composition is a multielement oxide comprising the element Mo in the oxidized state.

Typically, such multielement oxides comprising Mo in the oxidized state are those multielement oxides which, as well as Mo, also comprise at least one of the elements Bi, V, P and Fe in the oxidized state. In principle, the term multielement oxide means that the catalytically active oxide composition, as well as oxygen and Mo, also comprises at least one other element (generally more than one other element). Particularly frequently, useful catalytically active oxide compositions for the preceding gas phase partial oxidation are those (especially Mo-containing) which comprise more than one metallic element, especially transition metal element. In this case, reference is made to multimetal oxide compositions. In general, catalytically active multielement oxide compositions (especially those which comprise Mo) are not simple physical mixtures of oxides of their elemental constituents, but rather heterogeneous mixtures of complex poly compounds of these elements.

The catalytically active composition of the catalysts of the fixed catalyst bed of a preceding gas phase partial oxidation (especially in the case of Mo-containing multielement oxide active compositions) are normally used shaped to shaped bodies of a wide variety of different geometries (as so-called geometric shaped catalyst bodies), in order to configure the fixed catalyst bed in the reaction tubes of the tube bundle reactor (to charge the reaction tubes with the fixed catalyst bed). For example, useful such geometric shaped bodies include spheres, tablets, extrudates, rings, spirals, pyramids, cylinders, prisms, cuboids, cubes, etc.

In the simplest case, the geometric shaped body may consist only of catalytically active composition which may, if appropriate, be diluted with shaping assistants and/or inert material. Such geometric shaped catalyst bodies are typically referred to as unsupported catalysts.

In the case of unsupported catalysts, the shaping can be effected, for example, by compacting the catalytically active powder material (for example a pulverulent multielement oxide active composition) to the desired catalyst geometry (for example by tableting, sintering or extruding). It is possible to add shaping assistants. Alternatively, a pulverulent precursor composition can be compacted to the desired catalyst geometry and the resulting geometric shaped body can be converted by thermal treatment (if appropriate in a molecular oxygen-comprising atmosphere) to the catalytically active multielement oxide shaped body (cf., for example, US 2005/0263926).

It will be appreciated that the shaping can also be effected in such a way that a geometric shaped body composed of catalytically inactive material (of inert material) is coated with active composition (also referred to hereinafter as "shaped support body" or as "support body" for short). Alternatively, it is also possible to coat with precursor composition and to convert to the active catalyst by subsequent thermal treatment (if appropriate in an atmosphere comprising molecular oxygen). In the simplest manner, the coating can be effected, for example, by moistening the surface of an inert support body by means of a liquid binder and subsequently adhering pulverulent active composition or pulverulent precursor composition on the moistened surface. The catalysts obtainable in this way are referred to as coated catalysts.

Suitable inert support bodies for many heterogeneously catalyzed partial gas phase oxidations are porous or nonporous aluminum oxides, silicon oxide, thorium dioxide, zirconium oxide, silicon carbide or silicates such as magnesium silicate or aluminum silicate (for example C220 steatite from CeramTec), but also metals, for example stainless steel or aluminum (cf., for example, US 2006/0205978).

Instead of coating the inert (inert here means generally that, when the reaction gas mixture is conducted through a catalyst tube charged only with inert support bodies under the reaction conditions, the conversion of the reactants is ≤5 mol %, usually ≤2 mol %) support body with pulverulent active composition or with pulverulent precursor composition, the support body can in many cases also be impregnated with a solution of the catalytically active substance or with a solution of a precursor substance and then the solvent can be volatilized and, if appropriate, a chemical reduction and/or thermal treatment (if appropriate in an atmosphere comprising molecular oxygen) can follow. The geometric shaped catalyst bodies which result in this way are typically referred to as supported or impregnated catalysts.

The longitudinal dimension L of such geometric shaped catalyst bodies (as is quite generally the case for geometric shaped bodies in this document) is understood to mean the longest possible direct line connecting two points on the surface of the shaped catalyst body. It is (also in the case of geometric shaped inert bodies) usually from 1 to 20 mm, often from 2 to 15 mm and in many cases from 3 or 4 to 10 or to 8 or to 6 mm. In the case of rings, the wall thickness is additionally typically from 0.5 to 6 mm, frequently from 1 to 4 or to 3 or to 2 mm.

The fixed catalyst bed does not consist of a bed of a single type of geometric shaped catalyst bodies which is uniform along the individual catalyst tube in all heterogeneously catalyzed partial preceding gas phase oxidations over the fixed catalyst bed disposed in the tubes of tube bundle reactors. Instead, the fixed catalyst bed, over the total length of the catalyst tube, can also consist of a homogenized mixture of a plurality of (i.e. at least two) mutually distinguishable types $S^i$ of geometric shaped catalyst bodies or of geometric shaped catalyst bodies and geometric shaped inert bodies (i.e. such a mixture may consist of at least two mutually distinguishable types of geometric shaped catalyst bodies, or of a single type of geometric shaped catalyst bodies and of a single type of geometric shaped inert bodies, or of at least two types of mutually distinguishable geometric shaped catalyst bodies and a single type of geometric shaped inert bodies, or of at least two types of mutually distinguishable geometric shaped catalyst bodies and at least two types of mutually distinguishable geometric shaped inert bodies). Possible distinguishing features of the different types $S^i$ are the type of geometry, the type of active composition, the type of support material, etc. Useful materials for the geometric shaped inert bodies include the same materials as have already been recommended for the inert geometric shaped support bodies for the coated catalysts and essentially do not intervene in the course of the gas phase partial oxidation. In principle, all inert shaped support bodies are also useful as geometric shaped inert bodies for diluting geometric shaped catalyst bodies in a fixed catalyst bed. Such a dilution allows the volume-specific activity of a fixed catalyst bed to be adjusted specifically to the requirement of the particular heterogeneously catalyzed partial gas phase oxidation.

The wording "homogenized mixture" means that measures have been taken in order to mix the different types of geometric shaped bodies (or the different longitudinal dimensions within one type) homogeneously with one another. In the ideal case, the homogeneous mixing along the entire longitudinal section attains the statistical average, also with regard to the particular individual type.

In many cases, a catalyst tube charge (a catalyst tube filling) with one fixed catalyst bed, however, also consists of a plurality of mutually distinguishable longitudinal sections installed alongside one another (in succession) (fixed catalyst bed (longitudinal) sections, catalyst bed sections). In this case, each individual longitudinal section may be configured uniformly over its length, as has already been detailed for a catalyst tube charged uniformly over its total catalyst tube length. At the transition from one intrinsically homogeneous bed section to the next intrinsically homogeneous bed section, the configuration (composition) of the bed changes abruptly. Along an individual catalyst tube, this gives rise to fixed catalyst beds which have a heterogeneous structure. Reference is also made to a structured filling (or bed) of the catalyst tubes. At the start (viewed in flow direction of the reaction gas flowing through the catalyst tube) and/or at the end of the catalyst tube, the fixed catalyst bed is frequently concluded by a sole bed of geometric shaped inert bodies.

Examples of such structured fillings of catalyst tubes are described, inter alia, in documents US 2006/0161019, EP-A 979 813, EP-A 090 744, EP-A 456 837, EP-A 1 106 598, U.S. Pat. No. 5,198,581 and U.S. Pat. No. 4,203,903.

In general, the filling of a catalyst tube with a structured fixed catalyst bed is configured such that the volume-specific activity of the fixed catalyst bed increases in flow direction of the fixed catalyst bed. The volume-specific activity of an intrinsically homogeneous longitudinal section of a fixed catalyst bed charge of a catalyst tube is increased when, with constant charging of the catalyst tube as in the corresponding longitudinal section of the catalyst tube under otherwise identical reaction conditions (i.e. identical composition of the reaction gas mixture, identical loading of the fixed catalyst bed charge with reaction gas mixture and identical entrance temperature of the heat carrier and identical flow conditions of the heat carrier), an increased reactant conversion (based on single pass of the reaction gas mixture through the catalyst tube) results.

The statements made in this document apply especially when the preceding fixed catalyst bed comprises at least shaped catalyst bodies (or consists only of such shaped catalyst bodies to an extent of at least 25%, or to an extent of at least 50%, or to an extent of at least 75%, or to an extent of 100% of its weight) whose active composition is a multielement oxide which comprises the element Mo in the oxidized state, with the proviso that the molar stoichiometric coefficient of the Mo within the elements of the multielement oxide active composition other than oxygen has the highest value.

All statements made in this document are valid especially when the preceding fixed catalyst bed comprises at least shaped catalyst bodies whose active composition is a multielement oxide of the general formula I $$Mo_{12}Bi_aFe_bX_c^1X_d^2X_e^3X_f^4O_n \quad (I)$$

where
$X^1$=nickel and/or cobalt,
$X^2$=thallium, an alkali metal and/or an alkaline earth metal,
$X^3$=zinc, phosphorus, arsenic, boron, antimony, tin, cerium, lead, vanadium, chromium and/or tungsten,
$X^4$=silicon, aluminum, titanium and/or zirconium,
a=0.2 to 5,
b=0.01 to 5,
c=0 to 10,
d=0 to 2,
e=0 to 8,
f=0 to 10, and
n=a number which is determined by the valency and frequency of the elements in I other than oxygen.

All statements made in this document are valid especially when the preceding fixed catalyst bed consists to an extent of at least 25%, or to an extent of at least 50%, or at least 75% of its weight, or only of shaped catalyst bodies whose active composition is a multielement oxide I (as always in this document, pure inert beds within the fixed catalyst bed are not taken into account in the calculation of the percentages by weight).

Preparation of corresponding (especially annular) unsupported catalysts and coated catalysts is described, for example, in US 2005/0263926, in DE-A 10313209, in WO 02/30569, in WO 2005/030393, in Research Disclosure RD 2005/497012, in DE-A 102007005606 and in DE-A 102007004961 (and the prior art cited in these documents).

The aforementioned documents and US 2006/0161019 recommend such (especially annular) shaped catalyst bodies especially for a heterogeneously catalyzed partial preceding gas phase oxidation of propylene to acrolein or acrolein and acrylic acid, and of isobutene to methacrolein or methacrolein and methacrylic acid. EP-A 970942 recommends such shaped catalyst bodies in particular for a heterogeneously catalyzed ammoxidation of propylene to acrylonitrile, or of isobutene to methacrylonitrile, as the preceding gas phase partial oxidation.

A ring geometry particularly relevant for one of the aforementioned preceding gas phase partial oxidations in the case of multielement oxide (I) shaped unsupported catalyst bodies is, for example, the geometry E (external diameter)×I (internal diameter)×L (length, height)=5 mm×2 mm×3 mm.

Other multimetal oxide (I) unsupported catalyst ring geometries E×I×L favorable for preceding gas phase partial oxidations are the geometries 5 mm×2 mm×2 mm, or 5 mm×3 mm×3 mm, or 5.5 mm×3.5 mm×3 mm, or 6 mm×4 mm×3 mm, or 6.5 mm×4.5 mm×3 mm, or 7 mm×5 mm×3 mm, or 7 mm×3 mm×7 mm, or 7 mm×4 mm×7 mm.

Regarding the active compositions of the stoichiometry of the general formula I, the stoichiometric coefficient b is preferably from 2 to 4, the stoichiometric coefficient c preferably from 3 to 10, the stoichiometric coefficient d preferably from 0.02 to 2, the stoichiometric coefficient e preferably from 0 to 5 and the stoichiometric coefficient f advantageously from 0.5 or 1 to 10.

More preferably, the aforementioned stoichiometric coefficients are simultaneously within the aforementioned preferred ranges.

Moreover, $X^1$ is preferably cobalt, $X^2$ is preferably K, Cs and/or Sr, more preferably K, $X^3$ is preferably tungsten, zinc and/or phosphorus, and $X^4$ is preferably Si. More preferably, the variables $X^1$ to $X^4$ each simultaneously have the aforementioned definitions.

All statements made in this document are additionally valid especially when the preceding fixed catalyst bed comprises at least shaped catalyst bodies whose active composition is a multielement oxide of the general formula II $$Mo_{12}P_aV_bX_c^1X_d^2X_e^3Sb_fRe_gS_hO_n \quad (II)$$

where
$X^1$=potassium, rubidium and/or cesium,
$X^2$=copper and/or silver,
$X^3$=cerium, boron, zirconium, manganese, niobium and/or bismuth,
a=0.5 to 3
b=0.01 to 3,
c=0 to or 0.2 to 3,
d=0 to or 0.01 to 2,
e=0 to 2,
f=0 to or 0.01 to 2,
g=0 to 1,
h=0 to or 0.001 to 0.5, and
n=a number which is determined by the valency and frequency of the elements in II other than oxygen.

All statements made in this document are valid especially when the preceding fixed catalyst bed consists to an extent of at least 25%, or to an extent of at least 50%, or to an extent of at least 75% of its weight or only of shaped catalyst bodies whose active composition is a multielement oxide II. Shaped catalyst bodies with a multielement oxide II as the active composition are suitable especially for a heterogeneously catalyzed partial preceding gas phase oxidation of organic $C_4$ compounds (for example of n-butane to maleic anhydride) and very particularly for one of methacrolein to methacrylic acid. For example, the procedure may be as described in EP-A 467144 and as described in DE-A 102007005606 (and as described in the prior art cited in these two documents).

The preparation of multielement oxide II shaped catalyst bodies is likewise found in the two aforementioned documents. For a heterogeneously catalyzed partial preceding gas phase oxidation of methacrolein to methacrylic acid, particular preference is given to annular shaped unsupported catalyst bodies where E×I×L=7 mm×3 mm×6.9 mm (or ×7.0 mm).

All statements made in this document are also valid especially when the preceding fixed catalyst bed comprises at least shaped catalyst bodies whose active composition is a multielement oxide of the general formula III $$V_1P_bMo_cX_d^1X_e^2O_n \quad \text{(III)}$$

where
$X^1$=at least one element from the group consisting of Fe, Bi, Co, Ni, Si, Zn, Hf, Zr, Ti, Cr, Mn, Cu, B, Sn and Nb,
$X^2$=K, Na, Rb, Cs and/or Tl,
b=0.9 to 1.5,
c=>0 to 0.2, preferably 0.0001 to 0.1,
d=0 to 0.1,
e=0 to 0.1, and
n=a number which is determined by the valency and frequency of the elements in III other than oxygen.

All statements made in this document are valid especially when the preceding fixed catalyst bed consists to an extent of at least 25%, or to an extent of at least 50%, or to an extent of at least 75% of its weight, or only of shaped catalyst bodies whose active composition is a multielement oxide III.

Shaped catalyst bodies having a multielement oxide III as the active composition are suitable especially for the heterogeneously catalyzed partial gas phase oxidation of hydrocarbons having at least 4 carbon atoms (especially n-butane, n-butenes and/or benzene) to maleic anhydride as the preceding gas phase partial oxidation.

Advantageously, they are annular unsupported catalysts. Favorable ring geometries are, for example, E×I×L=6.6 mm×3.7 mm×4.2 mm or 5 mm×2.5 mm×3.2 mm. Otherwise, the partial oxidation process conditions recommended in the documents U.S. Pat. No. 5,011,945, WO1997/012674, WO 03/078310, WO 01/68245, DE-A 102005035978 and DE-A 102007005606 can be employed. The aforementioned documents also describe the preparation of multielement oxide (III) shaped catalyst bodies.

Moreover, all statements made in this document are valid especially when the preceding catalyst bed comprises at least one shaped catalyst body whose active composition is a multielement oxide of the general formula IV $$Mo_{12}V_aX_b^1X_c^2X_d^3X_e^4X_f^5X_g^6O_n \quad \text{(IV)}$$

where
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals (Li, Na, K, Rb, Cs) and/or H,
$X^5$=one or more alkaline earth metals (Mg, Ca, Sr, Ba),
$X^6$=Si, Al, Ti and/or Zr,
a=1 to 6,
b=0.2 to 4,
c=0 to 18, preferably 0.5 to 18,
d=0 to 40,
e=0 to 2,
f=0 to 4,
g=0 to 40 and
n=a number which is determined by the valency and frequency of the elements in IV other than oxygen.

All statements made in this document are valid especially when the preceding fixed catalyst bed consists to an extent of at least 25%, or to an extent of at least 50%, or to an extent of at least 75% of its weight, or only of shaped catalyst bodies whose active composition is a multielement oxide IV.

Shaped catalyst bodies having a multielement oxide IV as the active composition are suitable especially for the heterogeneously catalyzed partial gas phase oxidation of acrolein to acrylic acid as the preceding gas phase partial oxidation. Advantageously, the shaped catalyst bodies here are coated catalysts (especially annular), as obtainable, for example, according to DE-A 102004025445, DE-A 10350822, DE-A 102007010422, US 2006/0205978, EP-A 714700 and DE 102007010422.9, and the prior art cited in these documents. The active composition coating thickness may be from 10 to 1000 μm, preferably from 50 to 500 μm and more preferably from 150 to 250 μm. Favorable coating thicknesses here are in particular those of the exemplary embodiments of EP-A 714700. A preferred ring geometry is that where E×I×L=7 mm×4 mm×3 mm. The aforementioned documents and the prior art cited in these documents also describe the partial oxidation process conditions.

Moreover, the statements made in this document apply especially when the preceding fixed catalyst bed comprises at least shaped catalyst bodies whose multielement oxide is a multielement oxide which comprises, as elements other than oxygen, as well as the elements Mo and V, at least one of the two elements Te and Sb, and at least one of the elements from the group comprising Nb, Pb, Ta, W, Ti, Al, Zr, Cr, Mn, Ga, Fe, Ru, Co, Rh, Ni, Pd, Pt, La, Bi, B, Ce, Sn, Zn, Si, Na, Li, K, Mg, Ag, Au and In in combination (in this case, the proportion by weight of such shaped catalyst bodies in the fixed catalyst bed may be at least 25%, or at least 50%, or at least 75%, or else 100% of the weight of the fixed catalyst bed).

They can be prepared, for example, as described on pages 25, 26 of WO 2004/108267.

The combination preferably comprises, from the latter group of elements, the elements Nb, Ta, W and/or Ti and more preferably the element Nb.

The aforementioned multielement oxide compositions preferably comprise the aforementioned element combination in the stoichiometry V, $$Mo_1V_bM_c^1M_d^2 \quad \text{(V)}$$

where
$M^1$=Te and/or Sb,
$M^2$=at least one of the elements from the group comprising Nb, Ta, W, Ti, Al, Zr, Cr, Mn, Ga, Fe, Ru, Co, Rh, Ni, Pd, Pt, La, Bi, Ce, Sn, Zn, Si, Na, Li, K, Mg, Ag, Au and In,
b=0.01 to 1,
c=>0 to 1, and
d=>0 to 1.

Preferably, $M^1$=Te and $M^2$=Nb, Ta, W and/or Ti. Preferably, $M^2$=Nb. The stoichiometric coefficient b is advantageously from 0.1 to 0.6. Correspondingly, the preferred range for stoichiometric coefficient c extends from 0.01 to 1 or from 0.05 to 0.4, and favorable values for d are from 0.01 to 1 or from 0.1 to 0.6. It is particularly favorable when the stoichiometric coefficients b, c and d are simultaneously within the aforementioned preferred ranges. The aforementioned is especially true when the active composition, with regard to its elements other than oxygen, consists of an aforementioned element combination.

These are then especially the multielement oxide active compositions of the general stoichiometry VI $$Mo_1V_bM_c^1M_d^2O_n \quad \text{(VI)}$$

where the variables are each as defined with regard to the stoichiometry V and n=a number which is determined by the valency and frequency of the elements in (VI) other than oxygen.

The preparation of such multielement oxide active compositions and the shaped catalyst bodies manufactured from them can be found, for example, in the documents DE-A 19835247, DE-A 10122027, DE-A 10051419, DE-A 10046672, DE-A 10122027 and DE-A 10119933.

They are suitable, inter alia, as catalysts for the heterogeneously catalyzed partial gas phase oxidation of acrolein to acrylic acid, of propane to acrolein and/or acrylic acid, of isobutane to methacrolein and/or methacrylic acid, and for the ammoxidation of propane to acrylonitrile and of isobutane to methacrylonitrile as the preceding gas phase partial oxidation (cf., for example, DE 102007010422.9, EP-A 1734030, EP-A 93846, EP-A 608838, EP-A 895809, DE-A 10122027, DE-A 19835247, EP-A 1254709, EP-A 1192987, EP-A 962253, EP-A 1262235, DE-A 10119933, DE-A 10051419, DE-A 10034825, DE-A 10046672, DE-A 10254278, DE-A 10033121, DE-A 10029338, DE-A 10248584).

In particular, the process according to the invention is found to be suitable when the preceding fixed catalyst bed comprises at least shaped catalyst bodies whose active composition is a mixture of a multielement oxide comprising the element Mo in the oxidized state (for example one of the general formulae (I) to (VI)) and at least one finely divided substance S selected from the group consisting of oxides of molybdenum and of compounds of molybdenum from which an oxide of molybdenum forms under the action of elevated temperature and molecular oxygen. In preceding gas phase partial oxidations, such shaped catalyst bodies are generally notable for an improved lifetime (cf., for example, DE 10 2007 010 422.9).

The preceding fixed catalyst bed may consist of such shaped catalyst bodies to an extent of at least 25%, or to an extent of at least 50%, or to an extent of at least 75%, or to an extent of 100% of its weight.

In principle, the new heterogeneously catalyzed partial gas phase oxidation in the process according to the invention may be different from the preceding gas phase partial oxidation.

The same applies to the preceding fixed catalyst bed and the new fixed catalyst bed. Equally, the active composition of the shaped catalyst bodies of the new fixed catalyst bed need not necessarily comprise Mo.

In general, the new heterogeneously catalyzed partial gas phase oxidation in the process according to the invention will, however, be the same gas phase partial oxidation as (or a similar gas phase partial oxidation to) the preceding gas phase partial oxidation. In this case, all statements made in this document with regard to the preceding gas phase partial oxidation also apply in a corresponding manner to the new heterogeneously catalyzed partial gas phase oxidation, and the new fixed catalyst bed may in this case be of the same type as the preceding fixed catalyst bed. This fact is typically caused by virtue of a tube bundle reactor in many cases being designed in its detailed configuration so as to be adapted to a particular heterogeneously catalyzed preceding gas phase partial oxidation.

In principle, in the process according to the invention, the new heterogeneously catalyzed partial gas phase oxidation of an organic starting compound may, though, be any heterogeneously catalyzed partial gas phase oxidation of an organic starting compound (irrespective of the preceding gas phase partial oxidation).

Examples of such heterogeneously catalyzed partial oxidations of an organic starting compound include the conversion of methanol to formaldehyde (cf., for example, CH-A 449600, CH-A 38828), the conversion of propene to acrolein and/or acrylic acid (cf., for example, DE-A 23 51 151), the conversion of tert-butanol, isobutene, isobutane, isobutyraldehyde or the methyl ether of tert-butanol to methacrolein and/or methacrylic acid (cf., for example, DE-A 25 26 238, EP-A 092 097, EP-A 058 927, DE-A 41 32 263, DE-A 41 32 684 and DE-A 40 22 212), the conversion of acrolein to acrylic acid, the conversion of methacrolein to methacrylic acid (cf., for example, DE-A 25 26 238), the conversion of o-xylene or naphthalene to phthalic anhydride (cf., for example, EP-A 522 871) and the conversion of butadiene to maleic anhydride (cf., for example, DE-A 21 06 796 and DE-A 16 24 921), the conversion of $C_4$ hydrocarbons (especially 1-butene, 2-butene, butadiene and/or n-butane) to maleic anhydride (cf., for example, GB-A 1 464 198 and GB-A 1 291 354), the conversion of indanes to anthraquinones (cf., for example, DE-A 20 25 430), the conversion of ethylene to ethylene oxide (cf., for example, EP-A 352 849, EP-A 352 850, EP-A 532 325, U.S. Pat. No. 5,155,242 and U.S. Pat. No. 5,262,551) or of propylene to propylene oxide (cf., for example, DE-B 12 54 137, DE-A 21 59 346, EP-A 372 972, WO 89/07101, DE-A 43 11 608), the conversion of propylene and/or acrolein to acrylonitrile (cf., for example, DE-A 23 51 151), the conversion of isobutene and/or methacrolein to methacrylonitrile (i.e. the term "partial oxidation" shall in this document also comprise partial ammoxidation, i.e. a partial oxidation in the presence of ammonia), the oxidative dehydrogenation of hydrocarbons (cf., for example, DE-A 23 51 151), the conversion of propane to acrylonitrile or to acrolein and/or acrylic acid (cf., for example, DE-A 101 31 297, EP-A 1 090 684, EP-A 608 838, DE-A 100 46 672, EP-A 529 853, WO 01/96270 and DE-A 100 28 582) etc.

The application therefore also comprises the performance of heterogeneously catalyzed partial gas phase oxidations of organic starting compounds in tube bundle reactors recharged by a process according to the invention. This is especially true when the gas phase partial oxidation is one of the aforementioned.

Finally, it should be emphasized once again that the process according to the invention is suitable in particular when the heterogeneously catalyzed partial preceding gas phase oxidation is one of propylene to acrolein and/or acrylic acid, or of acrolein to acrylic acid, or of isobutene to methacrolein and/or methacrylic acid, or of methacrolein to methacrylic acid, or of propane to acrolein and/or acrylic acid, or of isobutane to methacrolein and/or methacrylic acid, or of propylene to acrylonitrile, or of propane to acrylonitrile, or of isobutene to methacrylonitrile, or of isobutane to methacrylonitrile, or of one or more $C_4$ hydrocarbons to maleic anhydride, or of methanol to formaldehyde.

This is especially true when the fixed catalyst bed comprises one of the multielement oxide active compositions of the general formulae I to VI.

The process according to the invention enables, over operating times of tube bundle reactors of several years, the reproducible recharging of its reaction tubes (with the best possible homogeneity of charging over all reaction tubes) and, on this basis, target product preparation with maximum selectivity of target product formation.

The process according to the invention is therefore directed not least to a process for maintaining a heterogeneously catalyzed partial gas phase oxidation of an organic compound which has been performed in the fixed catalyst bed disposed in the reaction tubes of a tube bundle reactor, the fixed catalyst bed having comprised at least shaped catalyst bodies whose active composition is a multielement oxide comprising the element Mo in the oxidized state and a steam-comprising product gas mixture having been obtained, wherein the fixed catalyst bed is removed from the reaction tubes of the tube bundle reactor and, in at least some of the reaction tubes, the solid deposit which comprises molybdenum oxide and/or molybdenum oxide hydrate and has been deposited on their inner wall is brushed away at least partly with the aid of a brush. Otherwise, both the charging of the reaction tubes with preceding fixed catalyst bed and with new fixed catalyst bed can be performed as described in DE 102007017080.9.

In principle, the process according to the invention can also be employed when the preceding fixed catalyst bed does not comprise any shaped catalyst bodies whose active composition is a multielement oxide comprising the element Mo in the oxidized state, but the reaction gas input mixture of the partial preceding gas phase oxidation comprises the steam-comprising product gas mixture of an upstream heterogeneously catalyzed partial gas phase oxidation of an organic compound whose fixed catalyst bed comprises shaped catalyst bodies whose active composition is a multielement oxide comprising the element Mo in the oxidized state.

EXAMPLE 1

Working example using a two-stage heterogeneously catalyzed partial gas phase oxidation of propylene to acrylic acid in two one-zone tube bundle reactors arranged in series.

Both tube bundle reactors were charged with fresh fixed catalyst beds. After the fixed catalyst beds had been formed, the steady-state operating conditions were as follows:

A) Description of the General Process Conditions

I. The First Reaction Stage
Heat exchange medium used: Salt melt consisting of 60% by weight of potassium nitrate and 40% by weight of sodium nitrite.
Material of the reaction tubes: Ferritic steel of DIN materials number 1.0481
Dimensions of the reaction tubes: length 3200 mm;
  internal diameter 25 mm;
  external diameter 30 mm (wall thickness: 2.5 mm).
Number of reaction tubes in the tube bundle: 25 500.
Reactor: Cylindrical vessel (ferritic steel of DIN materials number 1.0345) of an external diameter of 6800 mm; jacket wall thickness=1.8 cm in the middle part, thickened to 2.5 cm at the top and bottom; annular vertical tube bundle with a free central space.
  Diameter of the central free space: 1000 mm. Distance of the outermost reaction tubes from the vessel wall: 150 mm. Homogeneous reaction tube distribution in the tube bundle (6 equidistant neighboring tubes per reaction tube).
Reaction tube pitch: 38 mm.
The ends of the reaction tubes were secured with sealing into orifices of tube plates of plate thickness 125 mm and their orifices opened into a reactor hood which spans the upper reactor plate and is connected to the vessel at the upper end, and at the lower end into the cylindrical transition to the aftercooler.
The reactor hood which spans the upper reactor plate (the reactor plate E*) had an orifice E* (in the form of a gas inlet stub) with a diameter of 1020 mm.
The tube plates and the other elements of the tube bundle reactor were manufactured from ferritic steel of DIN materials number 1.0481. A thermocouple was admitted or introduced in each case into the reactor plate surface E* (at the outermost reaction tube circle) and into the upper reactor hood (the reactor hood E*). The upper reactor hood (total wall thickness=20 mm) was plated on the inside with stainless steel of the 1.4571 type (to DIN EN 10020) (plating thickness: 3 mm).
Feeding of the heat exchange medium to the tube bundle:
  The tube bundle was divided into 4 equidistant (in each case 730 mm) longitudinal sections (zones) by three deflecting disks (thickness in each case 10 mm) mounted successively between the tube plates in the longitudinal direction thereof.

The lowermost and the uppermost deflecting disk had ring geometry with an internal ring diameter of 1000 mm, and the external ring diameter extended up to and was sealed to the vessel wall. The reaction tubes were secured on the deflecting disks without sealing. Instead, gaps having a gap width of <0.5 mm were left such that the transverse flow rate of the salt melt within one zone was substantially constant.

The middle deflecting disk was circular and extended up to the outermost reaction tubes of the tube bundle.

The circulation of the salt melt was accomplished by two salt pumps, each of which supplied one half of the tube bundle length.

The pumps injected the salt melt into an annular channel mounted around the reactor jacket at the bottom, which distributed the salt melt over the vessel circumference. The salt melt passed through windows present in the reactor jacket in the lowermost longitudinal section to the tube bundle. The salt melt then flowed, dictated by the deflecting plates, in the sequence
  from the outside inward,
  from the inside outward,
  from the outside inward,
  from the inside outward,
in an essentially meandering manner viewed over the vessel, from the bottom upward. The salt melt collected through windows mounted around the vessel circumference in the uppermost longitudinal section (the salt melt left the reaction tube surrounding space with the temperature $T_H^{1,out}$) in an upper annular channel mounted around the reactor jacket, and was, after cooling to the original entrance temperature $T_H^{1,in}$, injected back into the lower annular channel by the pumps.

The reaction gas entry mixture 1 was a mixture of air, chemical-grade propylene and cycle gas (cycle gas is the gas which remains after the target product removal from the product gas mixture of the two-stage heterogeneously catalyzed partial oxidation).
Reactor charge: Salt melt and reaction gas mixture were conducted in countercurrent viewed over the reactor. The salt melt entered at the bottom, the reaction gas mixture via the orifice E* at the top.
The entrance temperature of the salt melt was $T_H^{1,in}$.
The exit temperature of the salt melt was $T_H^{1,out}$.
$T_H^{1,out} - T_H^{1,in}$ was >0 and ≤2° C.
The pump output was 6200 m$^3$ of salt melt/h.
The reaction gas entry mixture 1 was fed to the reactor with a temperature of $T_G^{E*,1}$ when it passed through the orifice E*.
Propylene loading of the fixed catalyst bed 1: It was $L^1$ 1 (STP)/(l·h).
Reaction tube charge with fixed catalyst bed 1
(from the top downward): Zone A: 50 cm
  Preliminary bed of steatite rings of geometry 7 mm×3 mm×4 mm (external diameter×length×internal diameter)
Zone B: 100 cm
  Catalyst charge with a homogeneous mixture of 30% by weight of steatite rings of geometry 5 mm×3 mm×2 mm (external diameter×length×internal diameter) and 70% by weight of an annular unsupported catalyst which, like unsupported catalyst EUC 3 from WO 2005/030393, has been prepared using TIMREX T 44 from Timcal AG (Bodio, Switzerland) as auxiliary graphite and, without taking account of graphite still present, had the stoichiometry $Mo_{12}Bi_1W_2Co_{5.5}Fe_{2.94}Si_{1.59}K_{0.08}O_x$ with the ring geometry E×L×I×=5 mm×3 mm×2 mm.

Zone C: 170 cm

Catalyst charge only with the annular (5 mm×3 mm×2 mm=external diameter×length×internal diameter) unsupported catalyst used for zone B.

Thermal tubes (they numbered 10 and were distributed uniformly in the central region of the tube bundle) were configured and charged as follows in order to monitor the temperature in the reaction tubes in a representative manner.

Each of the 10 thermal tubes had a central thermowell with 40 temperature measurement points (i.e. each thermal tube comprised 40 thermocouples which were integrated at different length into a thermowell and thus formed a multithermocouple with which the temperature could be determined simultaneously at different heights within the thermal tube).

20 of the 40 temperature measurement points in each case were present in the region of the first meter of the active section of the fixed catalyst bed (in flow direction of the reaction gas mixture).

The internal diameter of one thermal tube was 29 mm. The wall thickness and the tube material were configured as for the working tubes.

The external diameter of the thermowell was 10 mm.

The thermal tubes were filled as follows:

A thermal tube was filled with the annular unsupported catalyst from zone B. In addition, catalyst spall of longitudinal dimension from 0.5 to 5 mm obtained from the annular unsupported catalyst was filled into the thermal tube.

The catalyst spall was filled in homogeneous distribution over the entire active section of the fixed catalyst bed of the particular thermal tube such that the pressure drop of the reaction gas mixture in the course of passage through the thermal tube corresponded to that in the course of passage of the reaction gas mixture through a working tube (based on the active section of the fixed catalyst bed (i.e. excluding the inert sections), from 5 to 30% by weight of catalyst spall were required for this purpose in the thermal tube). At the same time the particular total fill height of active and inert sections in the working and thermal tubes was equalized and the ratio of total amount of active composition present in the tube to heat transfer area of the tube in working and thermal tubes was adjusted to essentially the same value.

II. The Intermediate Cooling

The acrolein-comprising product gas mixture 1 leaving the first reaction stage with a temperature corresponding to the salt melt entrance temperature $T_H^{1,in}$ was, for the purpose of intermediate cooling, conducted through a one-zone tube bundle heat exchanger made of ferritic steel and cooled with a salt melt composed of 60% by weight of potassium nitrate and 40% by weight of sodium nitrite, which was flanged directly onto the lower tube plate of the tube bundle reactor of the first reaction stage. The distance of the lower tube plate of the tube bundle reactor from the upper tube plate of the cooler was 10 cm. The salt melt and the product gas mixture were conducted in countercurrent viewed over the heat exchanger. The salt bath itself flowed in the same way as in the first-stage one-zone tube bundle fixed bed reactor in a meandering manner around the cooling tubes through which the product gas mixture 1 was passed. The length of the cooling tubes was 1.65 m, their internal diameter was 2.6 cm and their wall thickness was 2.5 mm. The cooling tubes numbered 8000. The external diameter of the heat exchanger was 6.8 m; the wall thickness corresponded to that of the reactor.

They were distributed uniformly over the cross section with homogeneous tube pitch.

Spirals of stainless steel whose cross section corresponded virtually to that of the cooling tubes were introduced into the entrance of the cooling tubes (in flow direction). Their length was from 700 mm to 1000 mm (alternatively, the cooling tubes can be filled with large inert material rings). They served to improve the heat transfer.

The acrolein-comprising product gas mixture 1 left the intermediate cooler with a temperature $T_G^{Z,out}$. Subsequently, compressed air (secondary air) having a temperature of 140° C. was added to it in such an amount that the oxygen content in the product gas mixture 2 was 3.0% by volume, which resulted in the composition of the reaction gas entry mixture 2 for the second reaction stage.

This was fed with its temperature $T_G^{E,2}$ into the orifice E of the upper reactor hood of the one-zone tube bundle tube fixed bed reactor of the second reaction stage.

III. The Second Reaction Stage

A one-zone tube bundle fixed bed reactor identical in design to that of the first stage except that it had an upper and a lower reactor hood was used. Its upper reactor plate is the reactor plate E.

The composition of the reaction gas entry mixture 2 consisted of the product gas mixture of the first reaction stage and the secondary air.

Reactor charge: Salt melt and reaction gas mixture were conducted in countercurrent viewed over the reactor. The salt melt entered at the bottom, the reaction gas mixture at the top.

The entrance temperature of the salt melt was $T_H^{2,in}$. Its exit temperature was $T_H^{2,out}$.

$T_H^{2,out} - T_H^{2,in}$ was >0 and ≤2° C.

The pump output was 6200 m³ of salt melt/h.

The reaction gas entry mixture 2 was fed to the reactor with a temperature of $T_G^{E,2}$ when it passed through the orifice E.

The acrolein loading of the fixed catalyst bed 2: It was $L^2$ l (STP)/(l·h).

The reaction tube charge with fixed catalyst bed 2 (from the top downward) was: Zone A:

20 cm preliminary bed of steatite rings of geometry 7 mm×3 mm×4 mm (external diameter×length×internal diameter).

Zone B:

100 cm catalyst charge of a homogeneous mixture of 30% by weight of steatite rings of geometry 7 mm×3 mm×4 mm (external diameter×length×internal diameter) and 70% by weight of the annular (approx. 7 mm×3 mm×4 mm) coated catalyst $C_A$ from DE 10 2004 025 445 with the active composition $Mo_{12}V_3W_{1.2}Cu_{2.4}O_x$ and an active composition content of 20% by weight.

Zone C:

200 cm catalyst charge of the annular (approx. 7 mm×3 mm×4 mm) coated catalyst from zone B.

Thermal tubes (they numbered 10 and were distributed uniformly in the central region of the tube bundle) were configured and charged as follows in order to monitor the temperature in the reaction tubes in a representative manner.

Each of the 10 thermal tubes had a central thermowell with 40 temperature measurement points (i.e. each thermal tube comprised 40 thermocouples which were integrated at different length into a thermowell and thus formed a multithermocouple with which the temperature could be determined simultaneously at different heights within the thermal tube).

20 of the 40 temperature measurement points in each case were present in the region of the first meter of the active section of the fixed catalyst bed (in flow direction of the reaction gas mixture).

The internal diameter of one thermal tube was 29 mm. The wall thickness and the tube material were configured as for the working tubes.

The external diameter of the thermowell was 10 mm.

The thermal tubes were filled as follows:

A thermal tube was filled with the annular coated catalyst prepared. In addition, two geometries of spherical coated catalysts were filled into the thermal tube (same active composition as the annular coated catalyst; the diameter of the two types of steatite C220 (CeramTec) support spheres was 2-3 mm and 4-5 mm; the active composition content in both cases was 20% by weight; the preparation was effected as described for the annular coated catalyst, except that the binder was a corresponding amount of water).

The spherical coated catalysts were filled in homogeneous distribution over the entire active section of the fixed catalyst bed of the particular thermal tube such that the pressure drop of the reaction gas mixture when it passed through the thermal tube corresponded to that when the reaction gas mixture passed through a working tube (based on the active section of the fixed catalyst bed (i.e. excluding the inert sections), a total of from 5 to 40% by weight of the spherical coated catalysts were required for this purpose in the thermal tube). At the same time, the particular total fill height of active and inert sections in the working and thermal tubes was equalized and the ratio of total amount of active composition present in the tube to heat transfer area of the tube in working and thermal tubes was adjusted to the same value.

The product gas mixture 2 obtained in the second reaction stage was conducted out through the lower reactor hood of the tube bundle reactor and sent to its workup.

The conversion was monitored and controlled in the two reaction stages with reference to the residual propylene and acrolein contents in the product mixture 2.

L1 was selected to be 130 l (STP)/l·h. The composition of the reaction gas input mixture was:

6.0% by volume of propylene,
10.4% by volume of $O_2$,
1.4% by volume of $H_2O$,
0.4% by volume of CO,
0.9% by volume of $CO_2$ and
80.9% by volume of $N_2$.

$T_H^{1,in}$ was 328° C. $T_H^{2,in}$ was 270° C. $T_G^{E*,1}$ was 300° C. and $T_G^{E,2}$ was 240° C. $L^2$ was 93 l (STP)/l·h. The propylene conversion $C^P$ was 95 mol % (based on single pass of the reaction gas mixture through the two reaction stages) and the acrolein conversion $C^{Ac}$ was 99.4 mol % (likewise based on a single pass of the reaction gas mixture). The selectivity of acrylic acid formation $S^{AA}$ was 92 mol % based on converted propylene.

This two-stage gas phase partial oxidation was operated under essentially uniform conditions ($T_H^{1,in}$ and $T_H^{2,in}$ were increased gradually in order to maintain $C^P$ and $C^{Ac}$; according to WO 2005/042459, intermediate regenerations of the fixed catalyst beds were performed) over a period of four years. After four years of operating time, $T_H^{1,in}$ was 348° C. and $T_H^{2,in}$ was 299° C.

The partial oxidation was then interrupted and the fixed catalyst bed was withdrawn in both reaction stages.

With the aid of a cylindrical tube brush with spiral head (cylinder length provided with brush head=100 mm; external diameter of the tube brush=24 mm; bristle length=8.5 mm; bristle material=DIN material 1.4571; bristle thickness=0.2 mm), all reaction tubes of the two tube bundle reactors were cleaned by brushes.

The analysis (atomic emission spectroscopy with inductively coupled plasma) of the deposit which was present on the reaction tube inner walls and had been brushed out of the reaction tubes of the first reaction stage showed the following proportions by weight for the elements other than oxygen:

C<0.5% by weight;
Co<0.32% by weight;
Fe 0.17% by weight;
Mo 65% by weight.

The ignition loss (3 h at 600° C. under air) of the deposited material brushed out was 0.5% by weight.

Calculated as $MoO_3$, 97.5% by weight of the deposit in the tube inner walls was molybdenum oxide.

An endoscopic inspection of the reaction tubes demonstrated their complete freedom from deposits on the tube inner surface after the brushing had ended.

The tubes of the tube bundle heat exchanger used for the purpose of intermediate cooling were cleaned by brushing in an analogous manner to the reaction tubes.

A recharge of the two tube bundle reactors after the performance of brushing with the same but fresh fixed catalyst beds, after the formation of the fixed catalyst beds had ended, gave rise to the identical operating data as after the above-described first charge of the two tube bundle reactors connected in series.

EXAMPLE 2

The procedure of Example 1 was repeated. However, the internal diameter of the reaction tubes of the first reaction stage was 21 mm, their number was 22 087 and the reactor external diameter was 5100 mm. Moreover, in the tube bundle reactor of the first reaction stage, the salt melt was conducted in simple countercurrent to the reaction gas in the reaction tubes. The reaction internals were adjusted correspondingly. The catalyst charge consisted, for a length of 270 cm, exclusively of the annular 5×3×2 mm unsupported catalyst. The tube bundle reactor of the first reaction stage further comprises two types of thermal tubes (five of each). The internal diameter of one type was 25 mm (external diameter of the thermowell=8 mm) and the internal diameter of the other type was 22.8 mm (external diameter of the thermowell=6 mm). Correspondingly, the number of reaction tubes in the second reaction stage was only 15 649 with a reaction tube internal diameter of 25 mm. The external diameter of the second-stage tube bundle reactor was likewise 5100 mm. The thermal tubes corresponded to those in the second reaction stage of Example 1. In the second-stage tube bundle reactor too, the salt melt was conducted in simple countercurrent to the reaction gas. The catalyst charge was as in Example 1. Otherwise, the procedure was essentially as in Example 1. In other words, after the partial oxidation had been stopped in the two reaction stages, the fixed catalyst bed was withdrawn. The reaction tubes of the second reaction stage were subsequently brushed with the brush type used in Example 1. For the purpose of brushing the reaction tubes of the first reaction stage, in contrast, a cylindrical tube brush with spiral head from Hommel Hercules Werkzeughandel, Heidelbergerstrasse 52, D-68519 Viernheim was used (external diameter of the brush=21 mm, cylinder length provided with brush head=100 mm). The designation of the brush was:

tube brush 6202-808525 diameter 21×100×160 mm, spiral 12" BSW, corrugated brass wire of diameter 0.2 mm as the head, single spiral.

Alternatively, it is also possible here to use a corresponding tube brush with stainless steel bristles, whose external diameter is only 20.8 mm.

U.S. Provisional Patent Application No. 60/941,385, filed Jun. 1, 2007, is incorporated into the present patent application by literature reference.

With regard to the abovementioned teachings, numerous changes and deviations from the present invention are possible. It can therefore be assumed that the invention, within the scope of the appended claims, can be performed differently from the way described specifically herein.

The invention claimed is:

1. A process for heterogeneously catalyzed partial gas phase oxidation, the process comprising
    (a) performing a heterogeneously catalyzed partial gas phase oxidation of an organic starting compound in a fixed catalyst bed to obtain a steam comprising product gas mixture wherein the fixed catalyst bed is disposed in the reaction tubes of a tube bundle reactor and comprises at least shaped catalyst bodies whose active composition is a multielement oxide comprising the element Mo in the oxidized state;
    (b) withdrawing the fixed catalyst bed from the reaction tubes, after the partial oxidation has ended;
    (c) at least partly brushing away in at least some of the reaction tubes, a solid film (solid deposit) comprising molybdenum oxide and/or molybdenum oxide hydrate and has been deposited on their inner wall is brushed away at least partly with the aid of a brush; and
    (d) recharging the reaction tubes of the tube bundle reactor with a new fixed catalyst bed for the purpose of performing a new heterogeneously catalyzed partial gas phase oxidation of an organic starting compound in the new fixed catalyst bed,
    wherein the process does not comprise blasting the reaction tubes.

2. A process for maintaining a heterogeneously catalyzed partial gas phase oxidation of an organic compound which has been performed in the fixed catalyst bed disposed in the reaction tubes of a tube bundle reactor, the fixed catalyst bed having comprised at least shaped catalyst bodies whose active composition is a multielement oxide comprising the element Mo in the oxidized state and a steam-comprising product gas mixture having been obtained, wherein the fixed catalyst bed is removed from the reaction tubes of the tube bundle reactor and, in at least some of the reaction tubes, the solid deposit which comprises molybdenum oxide and/or molybdenum oxide hydrate and has been deposited on their inner wall is brushed away at least partly with the aid of a brush.

3. The process according to claim 1, wherein the brush is a cylindrical tube brush.

4. The process according to claim 1, wherein the brush is a cylindrical tube brush with a spiral head.

5. The process according to claim 1, wherein the solid deposit brushed away from the inner wall of the reaction tubes is sucked out of the reaction tubes as soon as it is formed.

6. The process according to claim 1, wherein the heterogeneously catalyzed partial preceding gas phase oxidation is one of
    propylene to acrolein and/or acrylic acid,
    acrolein to acrylic acid,
    isobutene to methacrolein and/or methacrylic acid,
    methacrolein to methacrylic acid,
    propane to acrolein and/or acrylic acid,
    isobutane to methacrolein and/or methacrylic acid,
    propylene to acrylonitrile,
    propane to acrylonitrile,
    isobutene to methacrylonitrile,
    isobutane to methacrylonitrile,
    one or more $C_4$ hydrocarbons to maleic anhydride, or
    methanol to formaldehyde.

* * * * *